(12) United States Patent
Jansson et al.

(10) Patent No.: US 12,036,374 B2
(45) Date of Patent: Jul. 16, 2024

(54) MEDICAL LINE TENSION MITIGATION SECUREMENT DEVICE

(71) Applicant: RoddyMedical, LLC, Wauwatosa, WI (US)

(72) Inventors: Kyle Jansson, Brookfield, WI (US); Patricia Deno, Dousman, WI (US)

(73) Assignee: RoddyMedical, LLC, Wauwatosa, WI (US)

( * ) Notice: Subject to any disclaimer, the term of this patent is extended or adjusted under 35 U.S.C. 154(b) by 0 days.

(21) Appl. No.: 17/942,100

(22) Filed: Sep. 9, 2022

(65) Prior Publication Data

US 2023/0310808 A1 Oct. 5, 2023

Related U.S. Application Data

(63) Continuation of application No. PCT/US2022/029348, filed on May 14, 2022.

(60) Provisional application No. 63/325,671, filed on Mar. 31, 2022.

(51) Int. Cl.
*A61M 25/02* (2006.01)

(52) U.S. Cl.
CPC ..... *A61M 25/02* (2013.01); *A61M 2025/0206* (2013.01); *A61M 2025/024* (2013.01); *A61M 2209/088* (2013.01)

(58) Field of Classification Search
CPC .......... A61M 25/02; A61M 2025/0206; A61M 2025/024; A61M 2209/088; A61M 5/1418; A61M 2025/026; A61M 2025/028; A61M 2025/0253; A61M 2005/1586; A61M 2025/0213; A61M 2025/0273; A61M 3/027; A61M 3/0266; A61M 25/01; A61M 16/0434; A61M 16/044; A61M 16/0481; A61M 16/0445; A61M 16/0459; Y10S 128/26; H02G 3/32
See application file for complete search history.

(56) References Cited

U.S. PATENT DOCUMENTS

| | | | |
|---|---|---|---|
| 3,630,195 A | 12/1971 | Santomieri | |
| 4,193,174 A * | 3/1980 | Stephens | A61M 39/28 128/207.18 |
| 4,606,735 A | 8/1986 | Wilder et al. | |
| 4,711,636 A | 12/1987 | Bierman | |
| 5,046,624 A | 9/1991 | Murphy | |
| D347,060 S | 5/1994 | Bierman | |
| 5,316,246 A | 5/1994 | Scott et al. | |
| 5,334,186 A | 8/1994 | Alexander | |

(Continued)

OTHER PUBLICATIONS

Rutledge et al., Catheter securement systems: comparison of two investigational devices to a sutureless securement device, a securement, 2015, Intensive Care Medicine Experimental, 3:24, pp. 1-14 (Year: 2015).*

(Continued)

*Primary Examiner* — Dung T Ulsh

(57) ABSTRACT

The invention relates to an apparatus, system and method to mitigate lines, tubes, and cords that are attached to a secure structure, such as a patient, from being displaced or pulled out from the insertion site of each line, tube, and cord on the patient when each line, tube and cord is pulled or yanked unexpectedly, as can routinely occur during patient movement, treatment, or therapy in a hospital, medical, or other environment.

24 Claims, 10 Drawing Sheets

(56) References Cited

U.S. PATENT DOCUMENTS

| | | | |
|---|---|---|---|
| 5,336,179 A | 8/1994 | Ryan | |
| D378,408 S | 3/1997 | Pyeatt | |
| D379,509 S | 5/1997 | Macko | |
| 5,876,371 A | 3/1999 | Yokoyama et al. | |
| D415,408 S | 10/1999 | Wizikowski, Sr. | |
| D425,987 S | 5/2000 | Goldstein | |
| 6,382,568 B1 | 5/2002 | Snell | |
| 6,458,104 B2 | 10/2002 | Gautsche | |
| 6,578,576 B1* | 6/2003 | Taormina | A61M 16/0497 128/207.14 |
| D479,328 S | 9/2003 | Reynolds et al. | |
| 7,284,729 B2 | 10/2007 | Walsh et al. | |
| 7,320,681 B2 | 1/2008 | Gillis et al. | |
| D568,254 S | 5/2008 | Patchett | |
| 8,020,825 B2 | 9/2011 | Dostaler et al. | |
| D657,460 S | 4/2012 | Uhlenkamp | |
| D657,869 S | 4/2012 | Mammen | |
| D677,557 S | 3/2013 | Drake | |
| 8,998,151 B2 | 4/2015 | Hoek | |
| D733,544 S | 7/2015 | Baur et al. | |
| D755,043 S | 5/2016 | Bailey | |
| D778,715 S | 2/2017 | Deachin | |
| 9,638,354 B1 | 5/2017 | Ogueli et al. | |
| D829,908 S | 10/2018 | Wonderley | |
| D837,367 S | 1/2019 | Reaux | |
| D837,374 S | 1/2019 | Wonderley | |
| 10,583,242 B2 | 3/2020 | Corato et al. | |
| D889,252 S | 7/2020 | Seiler | |
| D967,778 S | 10/2022 | Salditch | |
| D969,311 S | 11/2022 | Jansson | |
| D1,000,609 S | 10/2023 | Jannson | |
| D1,000,610 S | 10/2023 | Jannson | |
| 2003/0132352 A1 | 7/2003 | Weaver | |
| 2004/0118982 A1 | 6/2004 | Shillings et al. | |
| 2005/0077436 A1 | 4/2005 | Nelson | |
| 2005/0182368 A1* | 8/2005 | Gillis | A61M 25/02 128/DIG. 26 |
| 2005/0188993 A1* | 9/2005 | Steeves | A61M 16/0497 128/207.14 |
| 2006/0113432 A1 | 6/2006 | Driskell | |
| 2007/0114339 A1 | 5/2007 | Winchester | |
| 2008/0294117 A1 | 11/2008 | Ware | |
| 2011/0054409 A1 | 3/2011 | Nishtala | |
| 2012/0216385 A1* | 8/2012 | Taylor | A61M 25/02 428/156 |
| 2013/0138044 A1 | 5/2013 | Schuman et al. | |
| 2014/0207072 A1* | 7/2014 | Nokes, Jr. | A61J 15/0061 604/179 |
| 2014/0252177 A1 | 9/2014 | Vera | |
| 2014/0330247 A1* | 11/2014 | Rosenberg | A61M 25/02 604/506 |
| 2015/0141962 A1 | 5/2015 | Collins et al. | |
| 2017/0087296 A1 | 3/2017 | Florence | |
| 2018/0154117 A1* | 6/2018 | Roberts | A61M 25/02 |
| 2018/0200485 A1 | 7/2018 | Braham | |
| 2018/0207416 A1* | 7/2018 | Roddy | A61M 39/24 |
| 2020/0306117 A1 | 10/2020 | Moudy | |
| 2021/0244904 A1 | 8/2021 | Perrie et al. | |

OTHER PUBLICATIONS

"Testo, Dominic, Why You Need Certified USP Class VI Silicones, Jun. 19, 2017, Specialty Silicone Products, Inc., p. 2" (Year: 2019).*
US ISA, Outgoing—PCT/ISA/210—International Search Report and Written Opinion of the International Searching Authority (ISA) for PCT Application No. PCT/US22/29348, Mailed Aug. 11, 2022.
DaVinci Medical, "IV Guard," <https://www.davincimedicalusa.com/iv-guard>, website accessed Dec. 3, 2020.
DaVinci Medical, "IV Guard," <https://86a59e88-9213-4200-aa1c-eddf5bf02d4d.filesusr.com/ugd/fc241c_88c7510765e04f7a9d9304fe35aa0fe6.pdf>, website accessed Dec. 3, 2020.
NewMediaWire, "Introducing the Perfect Gift for Nurses On Certified Nurses Day: The Easy View IV Tu be Separator!," <http://www.newmediawire.com/news/introd ucing-the-perfect-g ift-for-nurses-on-certified-nurses-day:-the-easy-view-iv-tube-separator-3090182 >, publicly available at least as early as Mar. 10, 2014.
Dynamic Diagnostics, Inc., "Guideline IV Line Organizer," <https://hellodynamic.com/products/guideline>, website accessed May 1, 2021.
JMC Global Technologies, "JanaBand," <https://www.janaband.net>, publicly available at least as early as Oct. 11, 2011.
IV Organizer, "The IV Tube Organizer," <https://ivorganizer.com/> publicly available at least as early as Oct. 16, 2013.
"Nurse Buddy Multiple IV Line Organizer Patent Pending USPTO," https://www.youtube.com/watch?v=T2GMDSq5sh8> publicly available at least as early as Sep. 27, 2012, accessed on Sep. 6, 2022.
Marketlab, "IV Line Holder," <https://www.marketlab.com/iv-line-holder/p/IVLineHolder/> publicly available at least as early as Jun. 12, 2015.
Haynes, et al., Managing Spaghetti Syndrome in Critical Care With a Novel Device: A Nursing Perspective, Critical Care Nurse, vol. 35, No. 6, pp. 38-45, Dec. 2015.
Xodus Medical, Inc., "Tube Holder Brochure," <https://web.archive.org/web/20101206190840/http://www.xodusmedical.com/downloads/Brochures/Tube-Holder.pdf> publicly available at least as early as Dec. 11, 2010.
NovoSci, "Pediatric Tubing Organizer," <https://catalog.novosci.us/item/all-categories/tmp-tubing- organizers/311033-000> website accessed Dec. 3, 2020.
The Beata Clasp, "Tubing, Line, and Drain Organizer," <http://www.beataclasp.com/Product.htm>, publicly available at least as early as Nov. 20, 2008.
Strip T's, "Sterile Adhesive Organizer," <https://www.kappsurgical.com/wp-content/uploads/2016/12/Kapp-Strip-Ts-FFS_2pg_for-web.pdf> webpage publicly available at least as early as Jun. 11, 2019.
Surge Cardiovascular, "Tubing Organizers," <https://surgecardiovascular.com/producl/tubing-organizers/> website accessed Dec. 3, 2020.
https://ae01.alicdn.com/kf/HTB1ahpQQVXXXXbkXFXXq6xXFXXXE/10pcs-Cable-Winder-Earphone-Cable-Organizer-Desktop-Wire-Storage-Charger-Cable-Cord-Holder-Clip-For-MP3.jpg, accessed Dec. 9, 2020.
Blitzwolf.com, https://www.blitzwolf.com/bg_os/other/upload_temp/products/original/201802/1519099246_17.jpg, accessed Dec. 9, 2020.
Walmart, https://i5.walmartimages.com/asr/edd171b9-6d34-4344-9b2c-9cccd7f73554_1.409de50178c9892a6ae354fc510820af.jpeg, accessed Dec. 9, 2020.
http://www.organizeit.com/images/desk-cable-organizer.jpg, accessed Dec. 9, 2020.
http://www.organizeit.com/images/desk-cord-organizer.jpg, accessed Dec. 9, 2020.
RoddyMedical, LLC, "Innovative Medical Device Development SecureMove-TLC" <http://www.roddymedical.com>, first published Jun. 2, 2021, website accessed Sep. 6, 2022.
WIPO, International Designs Bulletin No. 31/2021—Jun. 8, 2021, International Registration No. DM/212671, Published Aug. 6, 2021.
Medline Industries, L.P., Tubing Anchor, at p. 20, Copyright 2019, available at: https://punchout.medline.com/media/catalog/Docs/MKT/LIT045R_CAT_Centurion_Dressings_and _.pdf.
Stryker Medical, Line Management System (Accessory Clip)—FA64210, at p. 67, available at: https://techweb.stryker.com/Critical_Care/FL27/2_5/operation/2131-409-001B.pdf.
Whitney Medical Solutions, "TubeCaddy Frequently Asked Questions (FAQs)," <https://www.whitneymedicalsolutions.com/med-surg-solutions/tubecaddy-0>, website accessed May 1, 2021, publicly available at least as early as Feb. 9, 2017.
IVA, "IV Organization System," <https://www.behance.net/gallery/51967161/IVA>, website accessed Dec. 3, 2020.
Amanda Corley, Nicole Marsh, Amanda J Ullman and Claire M Rickard, Tissue adhesive for vascular access devices: who, what, where and when?, British Journal of Nursing (IV Therapy Supplement), vol. 26, No. 19, pp. S4-S17, 2017.

(56) References Cited

OTHER PUBLICATIONS

Jan Hitchcock and Louise Savine, Medical adhesive-related skin injuries associated with vascular access, British Journal of Nursing (IV Therapy Supplement), vol. 26, No. 8, pp. S4-S12, 2017.
Nancy Moureau, Impact and Safety Associated with Accidental Dislodgement of Vascular Access Devices: A Survey of Professions, Settings, and Devices, JAVA, vol. 23, No. 4, pp. 203-215, 2018.
Jean-Francois Timsit, Alexis Tabah and Olivier Mimoz, Update on prevention of intra-vascular accesses complications, Springer Nature, vol. 23, No. 4, pp. 203-215, Jun. 2022, https://doi.org/10.1007/s00134-022-06763-5.
Lineus Medical, Performance Testing of Peripheral IV Securement in a Clinically Simulated Environment, https://lineusmed.com/vascular-access-research, Accessed Apr. 29, 2023.
Ellen Benjamin, Lindsey Roddy and Karen K. Giuliano, Management of patient tubes and lines during early mobility in the intensive care unit, Human Factors in Healthcare, vol. 2, 2022, https://www.sciencedirect.com/science/article/pii/S2772501422000148?via%3Dihub.
Amanda J. Ullman, Marie Cooke, and Claire M. Rickard, Examining the Role of Securement and Dressing Products to Prevent Central Venous Access Device Failure: A Narrative Review, JAVA, vol. 20, No. 2, pp. 99-110, 2015.
San Del Cord Holder: Cord Holder, 100 PK, Grainger, [Post date unknown], [Site seen Aug. 15, 2023], Seen at URL: https://www.grainger.com/product/SANDEL-Cord-Holder-Cord-Holder-499A61 (Year: 2023).

\* cited by examiner

MEDICAL LINE TENSION MITIGATION SECUREMENT DEVICE

CROSS REFERENCE TO RELATED APPLICATIONS

PCT Application No. PCT/US22/29348, filed on May 14, 2022;

U.S. Provisional application No. 63/325,671, filed on Mar. 31, 2022

BACKGROUND OF THE INVENTION

1. Field of the Invention

Embodiments of the present disclosure relate generally to medical line tension mitigation and securement devices.

2. Background

Clinicians and patients currently have no tools or products that can prevent line pulls (including IV tubing, cables, cords and the like) or dislodgement from patient insertion sites when patients need to be mobilized. Currently in the USA, 19 million lines pull out annually, and this issue is under-reported. Mobilization includes transporting or moving patients; bed transfers; including clinicians moving around the patient or bed; patient tasks such as sitting up, standing, moving to a chair, walking to the bathroom; or performing rehabilitative therapy. Currently 64% of early mobility therapy in Intensive Care Unit (ICU) settings is spent detangling and securing lines.

Following invasive procedures or injury, early mobility therapy is one of the best ways of increasing the rate of healing. However, most patients with serious hospitalizations have multiple lines and cords and are connected to life saving medical equipment. During early mobility therapy, these connections pose real issues and barriers as patients experience discomfort, pain, and fear of significant injury. Once discomfort is felt, it is human nature to not repeat that same activity. So, if discomfort is felt from a line pulling on a line insertion site during therapy, the patient will not want to perform that therapy again which may hinder the patient's ability to heal. Or worse, lines are accidentally pulled out of a patient insertion site which may contain life support lines or diagnostic monitoring equipment required for life support. If a life support line is pulled out of an insertion site, patient death can occur unless emergency interventions are quickly and accurately performed. Several types of trauma, from mental fear, to physical pain, to the risk of death prevent the desire to perform the needed therapy that promotes healing.

Tapes or adhesives and sutured-in lines are the commonly used methods to secure lines at patient insertion sites onto patient skin. This has many drawbacks such as, nagging discomfort, skin tears, skin irritation, blemishes and skin infections. Adhesives provide only a minimal amount of strength to grip lines, between 4-9 lbs. (1.8-4.1 kg) of pull force can pull off typical adhesives. Clinicians have also used tape and medicine cups or tongue depressors to group IV lines and cords to bedrails or have used rolled up incontinence pads and taped IV lines to the pads and then pinned them to patient gowns for an attempt at minimal securement with limited success. Line pulls and pullouts are a known problem, and the mentioned solutions are the best that resourceful clinicians have come up with to attempt a means of controlling and providing some sort of safety to their patients. There is currently nothing available that is reliable, reusable, and will secure multiple IV lines, tubes and cords in a in single location while also providing tension mitigation of a pull force up to and over at least 9 lbs. (4.1 kg) of pull force applied to said line, tube, or cord.

SUMMARY OF THE INVENTION

It is the object of the invention to provide a device inserted between the attachment site of lines, tubes, or cords on a patient's body and the source of a pull force (such as by a tug or yank) on the lines, tubes, or cords, the device preventing displacement of each line, tube or cord at the patient attachment or insertion site, as can routinely occur during patient movement, treatment, or therapy in a hospital or medical environment.

Another object of the invention is to provide an apparatus that is comprised of a minimal quantity of parts which are easy to manufacture.

In accordance with a first embodiment, the invention relates to an apparatus which comprises an armband, a securement body attached to the armband, a securement strap configured to cause the securement body to displace, and a strap attached to the armband utilized to secure the armband to a secure structure, such as a patient, a bed, an IV pole, a crutch, etc. The securement body is configured to securely hold at least one line, tube, or cord and the strap may additionally secure at least one transducer or another device to the armband. Further, the armband is biocompatible with human skin and able to be worn by a patient for at least a day, but preferably up to or exceeding 30 days.

In accordance with a second embodiment, the securement body may secure a single line or multiple lines within a single securement body, further the the securement strap and securement body may be formed integral to each other.

In accordance with a third embodiment, the securement body may be a shape and material composition designed to provide mitigation of a specific amount of pull force, such as 9 lbs. (4.1 kg) or 20 lbs. (9.1 kg) or even 70 lbs. (31.8 kg) or more.

The invention also relates to a method for mitigating the undesired removal of lines, tubes, and cords attached to a patient beginning with securing the securement device with a securement strap, at least one grip channel, and at least one a flange, wherein the flange is extending toward the top of the securement body, around a secure structure, such as a patient's arm, in an orientation so the flanges and slots of the securement device are facing upward. Next, the patient attached lines, tubes, and cords at patient insertion sites are each attached to the securement device. Last, the securement body is put under compression causing each flange to touch the neighboring flange and each slot width to reduce, thereby securing the securement device to each line, tube and cord so if any of the secured lines, tubes, or cords are yanked or pulled, each line, tube, and cord inserted into the patient will remain in place at their insertion sites, unaffected, as the pull force from the yank or pull is mitigated by the device.

DETAILED DESCRIPTION OF THE INVENTION

For the following defined terms, these definitions shall be applied, unless a different definition is given in the claims or elsewhere in this specification. All numeric values are herein assumed to be modified by the term "about," whether or not explicitly indicated. The term "about," in the context of numeric values, generally refers to a range of numbers that one of skill in the art would consider equivalent to the recited value (e.g., having the same function or result). In many instances, the term "about" may include numbers that are rounded to the nearest significant figure. Other uses of the term "about" (e.g., in a context other than numeric values) may be assumed to have their ordinary and customary definition(s), as understood from and consistent with the context of the specification, unless otherwise specified.

For the following defined terms, these definitions shall be applied, unless a different definition is given in the claims or elsewhere in this specification. Although some suitable dimensions, ranges, and/or values pertaining to various components, features and/or specifications are disclosed, one of skill in the art, incited by the present disclosure, would understand desired dimensions, ranges, and/or values may deviate from those expressly disclosed.

As used in this specification and the appended claims, the singular forms "a", "an", and "the" include plural referents unless the content clearly dictates otherwise. As used in this specification and the appended claims, the terms "and" and "or" are generally employed in its sense including "and/or" unless the content clearly dictates otherwise. It is to be noted that in order to facilitate understanding, certain features of the disclosure may be described in the singular, even though those features may be plural or recurring within the disclosed embodiment(s). Each instance of the features may include and/or be encompassed by the singular disclosure(s), unless expressly stated to the contrary.

As used herein, the terms "lines," "tubing," "IV," and "cords" are intended to be interchangeable and mean any flexible medical grade material used to carry fluid, gas, information, or electricity.

Figure 1:
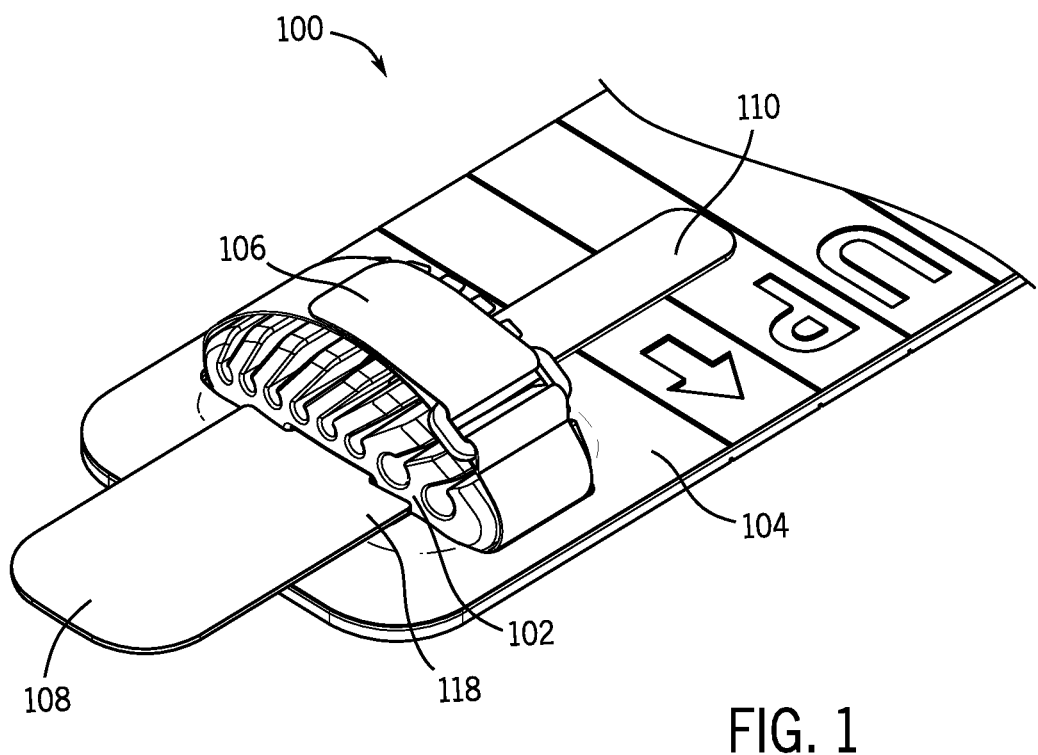
FIG. 1. is an enlarged rear perspective view of an embodiment of the present invention.
Figure 1:
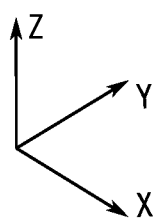

A medical line tension mitigation securement device, system, and method will now be described with references in FIGS. 1-13. Turning to the drawings, where the reference characters indicate corresponding elements throughout the several figures, attention is first directed to FIG. 1 where an enlarged rear perspective view of an embodiment of the present invention is shown, illustrating its composition, the apparatus is generally indicated by reference character 100. Medical line tension mitigation securement device 100 is designed to eliminate hazardous pulling and line or cord dislodgement from a patient during therapy, transport, and patient movement. Securement device 100 may be single use or reusable with the current embodiment being tested to operate effectively for up 30 days. Securement device 100 is configured to secure and organize one or more various sized and type of medical tubes, lines, and cords along a X, Y, and Z axis against pull forces along the X, Y, and Z axis. Securement device 100 is also designed to include a minimal set of components that are easily manufacturable and provide a much-needed solution to a recognized clinical problem, undesired tube or cord removal from patient insertion sites, potentially causing tube or cord attached equipment malfunction, patient pain and in some cases, death. The simplicity and optimization of securement device 100 is the outcome of 30+ iterations of design and thousands of hours of effort. Securement device 100 comprises a line securement body 102 comprised of a tacky elastomer material that is affixed to a flexible securement band 104, such as an armband (which will be used to refer to element 104, however it should be noted armband 104 is not limited to securement around a patient's arm). In the preferred embodiment line securement body 102 is permanently attached to armband 104 (such as by molding, adhesive, Velcro®, sewing, ultrasonic welding, or other methods), although it may be removable or adhered together using known methods to fix two or more dissimilar materials together. Securement device 100 further comprises a securement strap 106 wrapped around securement body 102, wherein securement strap 106 is configured to provide a variable amount of tension to securement body 102 while also preventing cords or lines held by securement body 102 from moving or being pulled out of the securement body (see FIG. 10). Additionally, securement device 100 further comprises a strap 118 which extends through securement body 102 and comprises a first end 108 configured to removably connect to armband 104 to tighten and secure armband 104 around a user's arm, or other secure structure, while strap 118 also comprises a second end 110 configured to secure to armband 104. Second end 110 may also be configured to secure at least one transducer (see FIG. 8 and FIG. 9), and preferably 3, to armband 104.

Armband 104 comfortably wraps around a secure structure, such as a patient's appendage, such as an arm or leg, much like a blood pressure cuff, and without adhesives. It should be noted that securement device 100, via armband 104, may be configured by subtle shape modifications to securement body 102, to mount to a patient other than by an arm or leg, such as the case with ECMO tubing, femoral catheters, Swan Ganz, oncology, labor and delivery, breathing tubing, Flight for Life, neo-natal ICU (NICU), military or other desired situations for line tension mitigation. Armband 104 can also be mounted to almost any rigid body, such as, but not limited to, an IV pole or bedrail and is intended to travel with the patient. Strap 118 is used to tightened and secure armband 104 around the arm, or other securement structure. Strap 118 must be properly secured with the appropriate tension to armband 104 in order to keep armband 104 from moving along the securement structure, such as a patient's arm, which may also require a different tension for each patient. It is contemplated the length and width of armband 104 may be varied to accommodate a specific patient characteristic, such as for bariatric, pediatric, or neonatal patients.

Figure 2:
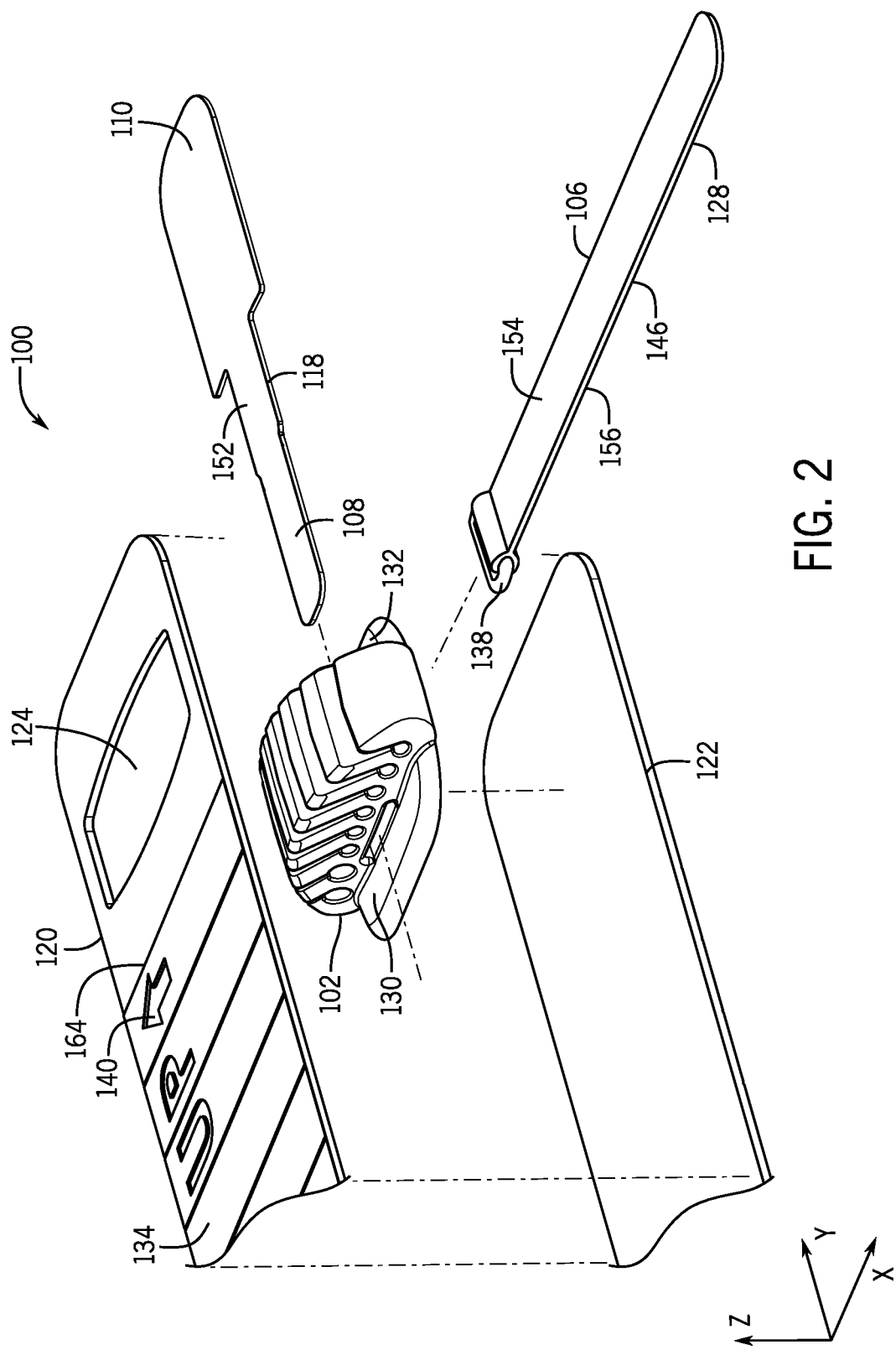
FIG. 2. is a front exploded view of an embodiment of the present invention.
Figure 3:
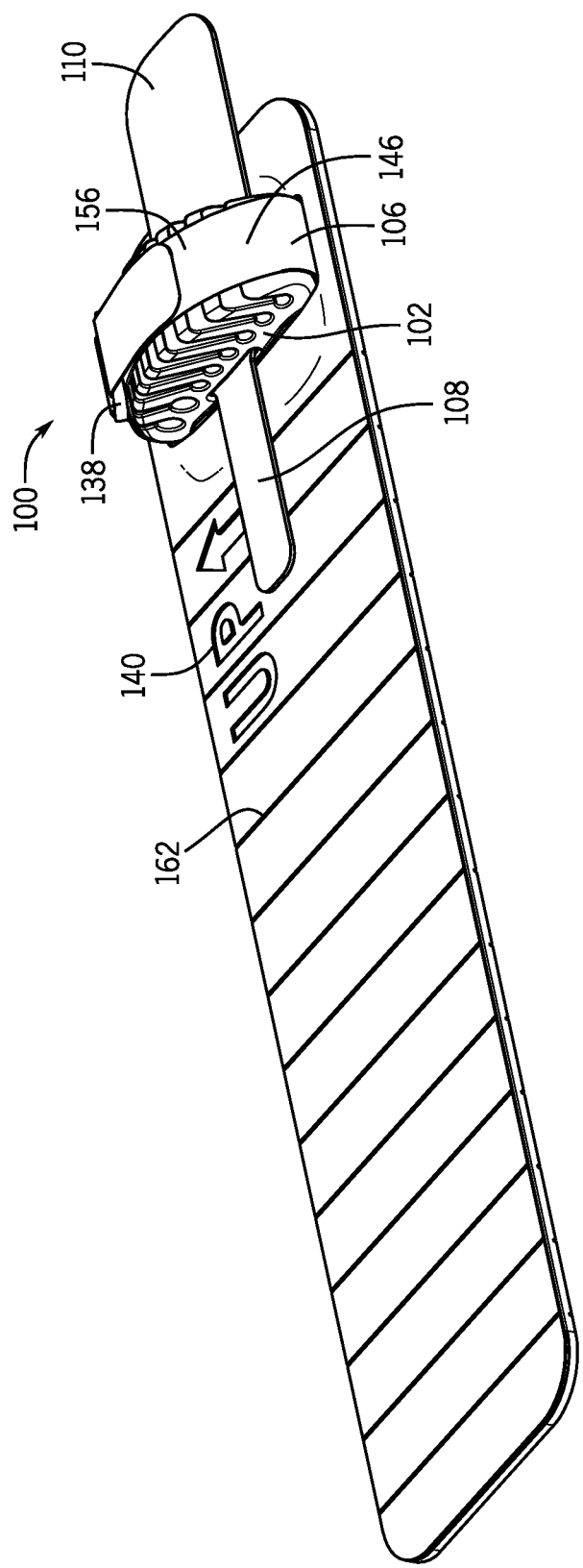
FIG. 3. is a perspective view of a fully assembled embodiment of the present invention.

Turning to FIG. 2 and FIG. 3, a front exploded view of an embodiment of the present invention and a perspective view of a fully assembled embodiment of the present invention is shown. Armband 104 is further comprised of at least an upper layer 120 with a body aperture 124 formed therethrough and configured to allow a portion of securement body 102 to extend through it wherein a portion of body 102 (base 112, first portion 130, and second portion 132 described below) remain below upper layer 120, and a lower layer 122 located below upper layer 120 and securement body 102, and an adhesive located between upper layer 120 and lower layer 122 (and the portion of securement body 102 between upper layer 120 and lower layer 122) to adhere the layers together (preferably permanently) with body 102, thereby securely sandwiching securement body 102 (via first portion 130 and second portion 132 described below) to armband 104. Body aperture 124 is the shape of the perimeter of securement body 102 without first protrusion 130 or second protrusion 132 (described below) of base 112 along the X and Y axis (in the XY-plane) (the perimeter of flanges 150, first termination end 114, and second termination end 116 described below), which is rectangular with rounded corners with the longest sides being curvilinear. Body aperture 124 is oriented to have its longest side extend across the width (X-axis) of armband 104, although aperture 124 may be located in an alternative location and position on armband 104 if desired to operate with securement body 102. Upper layer 120 is comprised of foam (or other flexible material such as fabric, plastic, etc.) with a top surface 134, wherein top surface 134 is covered with a loop fastener (not shown), such as Velcro®. Top surface 134 further comprises artwork 140 printed on, embossed with, or otherwise made viewable on top surface 134 of upper layer 120 to indicate the appropriate orientation of device 100 when securing to a patient. The orientation of securement body 102 is important for optimizing tube or cord securement during tugging as the orientation of securement body 102 attributes to the ability of securement device 100 to prevent cord or cable pullout from tugging from various directions (described more below). In the current embodiment, the artwork 140 includes the text "UP" with an arrow graphic is located near one edge of the top surface of upper layer 120 to indicate device 100 should be oriented so the artwork 140 is located closest to, and aiming towards the direction of a patient's head, or the top of the securement body. The direction coincides with the direction of securement body flanges 150 and corresponding slots 144 (discussed below). Armband 104 further comprises at least one score mark 164, but preferably a plurality, located across the width and in various locations along the length of upper layer 120 and lower layer 122 and configured to allow armband 104 to be flexible to easily wrap and secure around a secure structure.

Lower layer 122 is preferably comprised of a USP Class VI medical grade and skin biocompatible material configured to reduce or eliminate pressure sores which may develop on a patient from extended wearing of device 100, as well as provide a non-absorbent barrier against sweat and moisture. To apply armband 104 to a patient, armband 104 is applied around a patient's arm with direct skin contact, not over clothing. Lower layer 122 may also be comprised of foam (or other comfortable flexible material) and is configured to provide a useful amount of friction as to not slide freely along the surface of the skin (similar to the tension provided by flexible neoprene knee brace to remain in position) and does not require excessive tightening or retightening to stay in place. Armband 104 (via upper layer 120 and lower layer 122) in the current embodiment is about 17.75 in. (450.85 mm) long along the Y-axis and 4 in. (101.6 mm) wide along the X-axis with a score mark 164 located about every 1 inch (25.4 mm) along the length of armband 104 with the center of body aperture 124 located about 2 in. (50.8 mm) from one lengthwise end of armband 104.

Strap 118 is preferably comprised of Velcro® hook fastener material on at least one side with first end 108 being wider (about 1.88 in. (47.75 mm)) along the X-axis and longer (about 3 in. (76.2 mm)) along the Y-axis than second end 110 (about 0.75 in. (19.1 mm) wide along the X-axis by 2.75 in. (69.9 mm) long along the Y-axis in order to provide more surface area to adhere the hook fastener material of strap 118 to top surface 134 of upper layer 120, although the dimensions of first end 108 and second end 110 may be altered if desired. The hook fastener material of strap 118 faces toward top surface 134 of armband 104 to ensure removable adherence of strap 118 to armband 104. Strap 118 further comprises a middle portion 152 located in between first end 108 and second end 110 and has a length (along the X-axis) and width (along the Y-axis) less than the length and width of strap aperture 148 of securement body 102 (described below), however other dimensions as desired may be used. In the preferred embodiment middle portion is wider then first end 108, but can be the same width as first end 108 if preferred.

Figure 4:
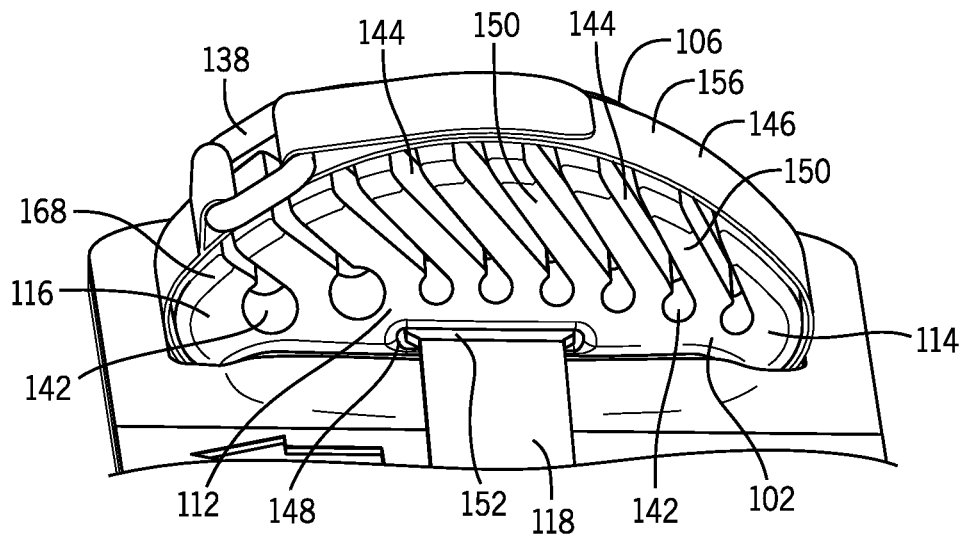
FIG. 4. is a front perspective view of an embodiment present invention.

Turning to FIG. 4, a front view of an embodiment of the present invention is shown. Line securement body 102 comprises a base 112 with a first termination end 114 connected on one side of base 112 and a second termination end 116 connected on the other side of base 112, and at least one securement flange 150, with seven shown in the present embodiment, located in-between (or sandwiched between) first termination end 114 and second termination end 116 and formed integral with and extending away from base 112, wherein each flange 150 is located in-line with one another and first termination end 114 and second termination end 116. Securement body 102 further comprises at least one grip channel 142 formed therethrough base 112 along the Y-axis and primarily circular or cylindrical in shape and configured to hold at least a portion of a tube, line, or cord. Other lines and cords besides IV lines may be inserted into similarly sized grip channels 142 such as oxygen tubes or electrical cables like pulse-oximetry lines, which are flexible but rigid radially and cannot be crushed like hollow fluid lines. These other lines or cords may be different sizes depending on the application as previously mentioned. Grip channel 142 is located between first termination end 114 and the at least one flange 150, between the at least one flange 150 and another flange 150, and between a flange 150 and the second termination end 116. Each grip channel 142 is further connected to a slot 144 which extends away from the grip channel 142, wherein slot 144 is configured to allow a tube, line, or cord to slide through said slot into the corresponding connected grip channel 142. Each slot 144 is defined by a flange 150 and another flange 150, a flange 150 and a first termination end 114, or a flange 150 and a second termination end 116. The overall shape of first line securement body 102 is purposefully curvilinear, in the XZ-plane, along the tops of first termination end 114, each flange 150, and second termination end 116 in order to utilize the concept of hoop stress (described below) to ensure securement body 102 adequately secures tubing within grip channels 142 by applying force to a held line or tube around the circumference of the held line or tube. Securement body 102 is also curvilinear shaped in the XY-plane (see FIG. 6) with the flange 150 located at the center point of body 102 the longest (along the Y-axis) with each subsequent flange 150 toward first termination end 114 and second termination end 116 reducing in length (along the Y-axis) to create a tapering effect (in part for at least ornamental design reasons) (see FIG. 6). Securement body 102 is symmetrically shaped along the XZ and XY-plane in the current embodiment. In addition, if there is more than one flange 150 attached to base 112, all of the flanges 150 may be varied lengths, preferably symmetrical along the X-axis about a central flange 150 that centrally located on securement body 102 and is the tallest as compared to the other flanges 150. In the current embodiment base 112 is about 3.13 in. (79.4 mm) in length (along the X-axis), and a width varying from about 1.5 in. (38.1 mm) at the center of base 112 length tapering to 1.25 in. (31.8 mm) wide at first termination end 114 and second termination end 116 (flanges 150 follow this width range as well with a thickness ranging from 0.125 in. (3.18 mm) to about 0.25 in. (6.35 mm) and slot 144 length varying between about 0.125 in. (3.18 mm) and 0.75 in. (19.05 mm)) however these dimensions may be altered if desired for such reasons as including, but not limited to: varying line quantity secured by securement body 102 (by changing grip channel 142 quantity), variation in force applied to secured lines, and variation in secured line diameter. Each slot 144 is preferably straight (as defined by two securement flanges 150 next to each other, a segment flange 150 and first termination end 114, or a flange 150 and second termination end 116) but can be curvilinear or varied in shape if desired (see FIG. 13). It is important to note that while grip channel 150 is preferably circular or cylindrical (to accommodate at least a portion of circular or cylindrical tubing) but could be other shapes to accommodate other shaped flexible tubing. The diameter of a grip channel 150 is specific for a specific range of IV-line, tubing, or cord diameters to ensure proper and optimal securement. While medical tube lines and cords do not follow standard size guidelines, there are similarities between manufacturers that are in a tight enough size range that an average nominal line size could be determined as common for significant enough sized tubes, lines, and cords to warrant a value to be used in creating a common grip channel 142 size to house each range of tubes, lines, and cords. There are an infinite range of lines, tubes, and cords as well, but the nominal grouping chose in the current embodiment is about ⅛" (or close to 3 mm) and about ¼" (or close to 6 mm). Each grip channel 142 in securement body 102 accommodates the width of slot 144 needed for manufacturability of securement body 102 (preferably via injection molding or other molding process) and to allow insertion of tubes matched to a particular grip channel 150 diameter so that the grip channel 150 size, when securement body 102 is in its constraining state, via tightening of securement strap 106, each slot 144 is closed or minimized by each flange 150, flange 150 and termination end 114 or 116 touching, so grip channel 142 matches this nominal ⅛" and ¼" diameter size so grip channel 142 touches the outer surface of the held tubing around its circumference. A secure fit of tubing to grip channel 142 is critical as the grip channel 142 size that most closely matches the tube, line, or cord will yield the greatest effect on restraining line tension (and preventing pullout of the tube in patient insertion sites). It is contemplated a grip channel 142 may comprise other nominal diameter sizes and line securement body 102 may contain any desired number of securement flanges 150 and thus grip channels 142 and slots 144 as desired for a specific application. Similarly, grip channel 142 should be as close to a circle in shape as possible to provide a uniform load around the held tubing to exhibit a strong grip all around the secured tubing and to prevent fluid restriction within the tubing. In the event that grip channel 142 is an oval, square, triangle, or anything besides a circle (assuming a circular tube is being held by grip channel 142), the gripping force exerted on tubing held within grip channel 150 will not be consistent around the circumference of the tubing and will thus be weaker than compared to a circle. First termination end 114 located on one end of secure body 102 (along the X-axis) and is generally curved or partially tear drop shaped on one side and may also comprise a flange 150, while second termination end 116 is located on the opposing end of secure body 102 (also along the X-axis) and is generally curved in the opposite direction as first termination end 114 and may include an extension 168 protruding in the opposing direction as flanges 150, wherein extension 168 helps to form a grip channel 150 and slot 144 between termination end 116 and neighboring flange 150.

If a pull force occurs (IV, line, tubing, or cord becomes tugged or yanked) on a line which has been secured to a grip channel 142 via compression of body 102 by securement strap 106, the pull force is mitigated at the device 100 by channeling the pull force from device 100 to the securement structure (patient's arm for example), leaving the patient's insertion site unaffected. Securement device 100 easily mitigates 20+ lbs. (9.1 kg) of pull force (see below for further description), and preferably up to 80+ lbs. of pull force. To give some context regarding the important of mitigating at least 20+ lbs. (9.1 kg) of pull force, central venous catheters can pull out with between just 4-9 lbs. (1.8-4.1 kg) of pull force. Further, due to the design of device 100, it does not crush or crimp lines, allowing for safe fluid flow even under significant gripping conditions.

Base 112 of securement body 102 further comprises a strap aperture 148 formed therethrough and configured to allow strap 118 to extend through strap aperture 148. Strap aperture 148 is positioned above upper layer 120 of armband 104 to allow movement of strap 118 through strap aperture 148 for various needs of a user (such as installing one or more transducers on first end of strap 118 or to provide additional length to armband 104 for a securement purpose. In the current embodiment strap aperture 148 is about 1 inch (25.4 mm) along the X-axis and about 1.5 in. (38.1 mm) along the Y-axis, however strap aperture 148 may be changed in size and configuration if desired. Strap aperture 148 is rectangular with rounded corners and about 0.0625 in. (1.59 mm) tall along the Z-axis, about 1 in. (25.4 mm) along the X-axis, and 1.56 in. (39.6 mm) along the Y-axis, but can be configured into a different shape and dimensions as desired.

Figure 5:
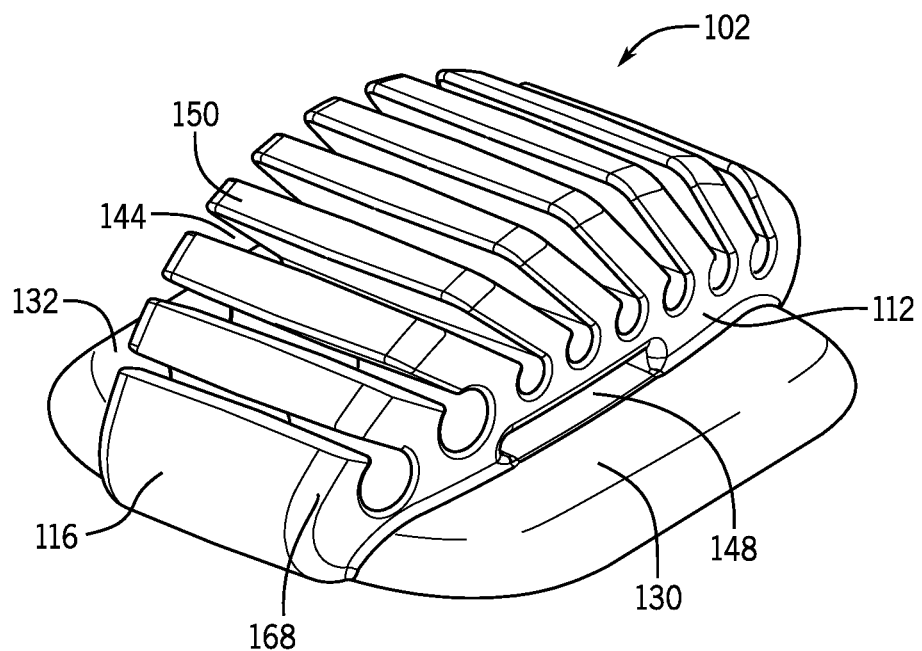
FIG. 5. is a perspective view of an embodiment of securement body 102.
Figure 6:
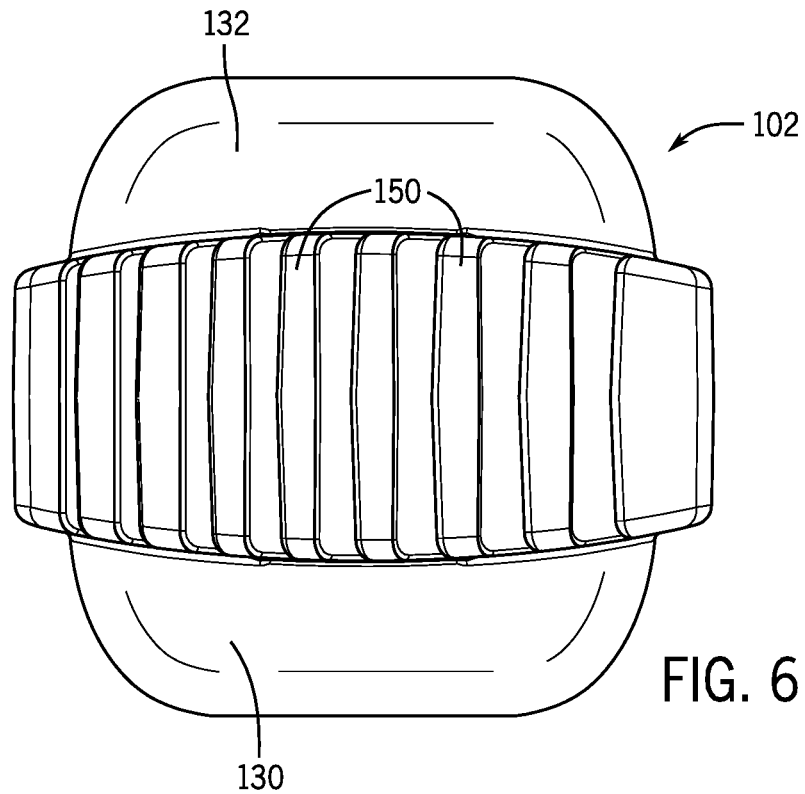
FIG. 6. is a top view of an embodiment of securement body 102.

Turning to FIG. 5 and FIG. 6, a perspective view and a top view of an embodiment of securement body 102 is shown. Securement body 102 further comprises a first protrusion 130 connected to base 112 and extending away from base 112 (along the Y-axis), perpendicular to each flange 150 and parallel to each grip channel 142, and a second protrusion 132 connected to base and extending away from base 112 (along the Y-axis), perpendicular to each flange 150 and parallel to each grip channel 142, wherein the second protrusion 132 is a mirror image of the first protrusion 130 and located on the opposite wall of first protrusion 130. Both first protrusion 130 and second protrusion 132 are generally rectangular with rounded corners but could be configured into a different shape and configuration as desired per other potential methods for optimal bonding to armband 104. First protrusion 130 and second protrusion 132 are configured to be sandwiched between upper layer 120 and lower layer 122 and secure securement body 102 to armband 104, preferably permanently. The securement of body 102 to armband 104 is important and significant to ensure device 100 can withstand the 20+ lbs. (9.1 kg) of pull force on secured tubing, lines, or cables within grip channels 142 and transfer the pull force to the securement body 102 the device 100 is attached to. Turning to FIG. 6, as mentioned above, the widths of flanges 150, first termination end 114, and second termination end 150 can vary, in the current embodiment they form a generally curvilinear shape. The bottom of base 112 is flat (although due to the material securement body 102 is produced from base 112 is flexible) in order to allow easy part measuring for improved quality assurance practices during molding/manufacturing and also to allow easy tooling to assemble and bond to upper layer 120 and lower layer 122 but is flexible enough to allow securement body 102 to deform when put under tension by securement strap 106, allowing flanges 150 overlap each other (and/or first termination end 114 and second termination end 116), slots 144 reduce in size, and grip channels 142 pressing against the portions of secured tubes secured within grip channels 142, causing securement body 102 becomes symmetrical or nearly symmetrical in shape along the XZ-plane, thus providing more uniform hoop stress (uniform compression forces/load applied around the circumference of the tubing portion held within securement body 102 which provides optimal tension mitigation by device 100 from tubing pull forces) on secured tubing within grip channels 142 (see. FIG. 7B).

Turning back to FIG. 2 and FIG. 4, securement strap 106 is comprised of a flexible material with a top surface 154, a bottom surface 156, and a buckle 138 fixed to one end. Securement strap 106 further comprises a hook fastener portion 128 located on bottom surface 156 located near the end of strap 106 opposite of buckle 138 and extending toward buckle 138, about 2.5 in. (25.4 mm) in the current embodiment (however other sizes may be used), and a loop fastener portion 146 also on the bottom surface 156 extending from buckle 138 to loop fastener portion 146, about 6.5 in. (165.1 mm), but can be other shapes as desired. It should be noted the width of securement strap 106 is important as the width of the current embodiment is about 1 inch (25.4 mm) and it has been found with the current size characteristics of securement body 102, a width of securement strap 106 less than 1 inch (25.4 mm) increases the pressure placed on secured lines in each grip channel 142 as compared to a securement strap 106 width of 1 inch (25.4 mm) with the same tension force (about 10 lbs. (4.5 kg) in the current embodiment), which can be useful in some embodiments. In use, securement strap 106 surrounds and tightens itself against securement body 102 in the XZ-plane, thereby causing flanges 150 to touch or overlap and securement body 102 to compress around tubing contained within each grip channel 142, thereby securing the tubing from moving within securement body 102 due to a yank or tug. Top surface 154 of securement strap 106 comes into slidable contact with the securement body 102 along the XZ-plane, and securement strap 106 threads through buckle 138 so that loop fastener portion 146 is in contact with hook fastener portion 128 at the desired tension, however it is contemplated at least a portion of securement strap 106 may be fixed to securement body 102 or armband 104. The tension securement strap 106 applies to securement body 102 is variable and dependent on the length of securement strap 106 threaded through buckle 138. While other types and brands of material may be used for loop fastener portion 146 and hook fastener portion 128, Velcro® brand is preferred. Further, securement strap 106 remains slidable between the bottom of base 112 and lower layer 122 of armband 104 to allow the variable tension to be applied to body 102. Securement strap 106 is ideally comprised of Velcro® but other securement strap methodologies known in the art may be employed, such as zip ties, a string, a clamp, a clasp, or an elastomer closure strap.

It was found during pull force testing of lines, tubes, and cords secured within securement device 100 that the direction of each slot 144 (and thus each flange 150), which allows insertion or removal of each line, poses a slight weakness in securement body 102 when a pull force is applied in the same direction and alignment as slot 144, even when securement body 102 is under compression by securement strap 106. So, as patients and their arms are statistically upright during sitting, standing, and therapy, each slot 144 and securement flange 150, when device 100 is secured to a patient, is configured to face upward, toward the top of the arm (or a person's head) in order to reduce the likelihood of a pull force on a line secured in device 100 along the direction of a slot since most line pulls are downward due to gravity (toward the floor). As such, each slot 144 are oriented in the least likely direction for a line pull to occur where maximum line securement retention exists. Additionally, the angle of the each securement flange 150 (and thus each slot 144) allows for each securement flange 150 to overlap the neighboring securement flange 150 or second termination end 116 (and to allow first termination end 114 to overlap neighboring flange 150) and provide a compressive load on any IV lines, tubes, or cords within each grip channel 142 when the securement strap 106 is tightened down (for example 10 lbs. (4.5 kg) of strap force may be adequate to provide at least 20 lbs. (9.1 kg) of pull force mitigation on a line or tube secured within a grip channel 142), rather than potential buckling of the line, tube, or cord if the each securement flange 150 (and thus each slot 144) were purely vertically (or perpendicular to base 112) oriented.

Figure 7A:
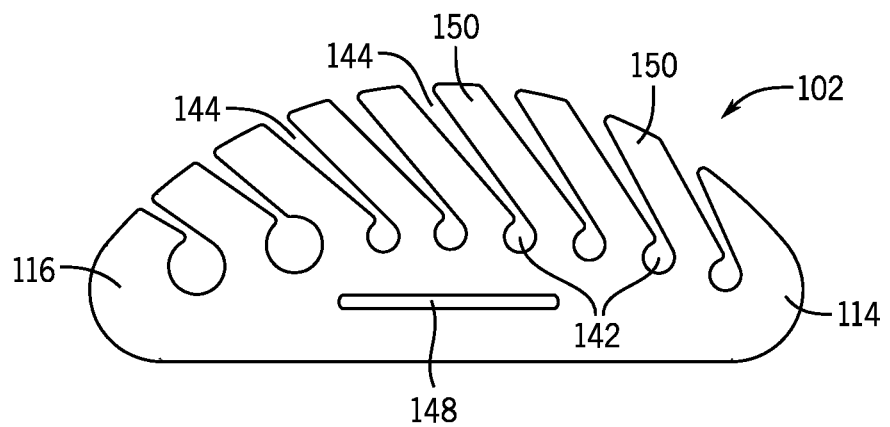
FIG. 7A. is a left side view of an embodiment of securement body 102 without first portion 130 and second portion 132 not shown before compression from securement strap 106.
Figure 7B:
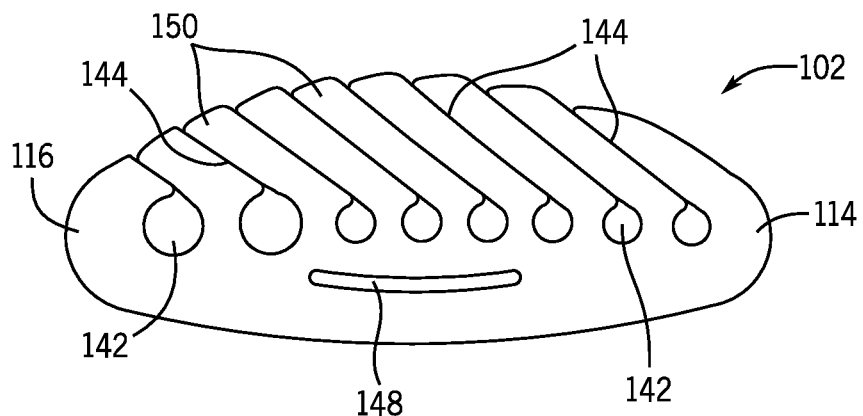
FIG. 7B. is a left side view of an embodiment of securement body 102 without first portion 130 and second portion 132 not shown after compression from securement strap 106.

Turning to FIGS. 7A and 7B, a a left side view of an embodiment of securement body 102 without first portion 130 and second portion 132 before compression from securement strap 106 and after compression by securement strap 106 (not shown) is shown. After numerous tests, the preferred angle of securement flange 150 to allow ease of cord insertion, cord removal, and maximum cord securement due to the uniform overlapping nature of flanges 150 over each other to secure lines within each grip channel 142 to transmit the compressive loads through the body when under load is between 20 and 50 degrees (in relation to base 112) without securement strap 106 tightened, and about 35 degrees (in relation to base 112) when the securement strap 106 is tightened, and compressive load is applied to any IV lines, tubes, or cords within each grip channel 150. It is contemplated the angle of each securement flange 150 may vary depending on what is desired to be secured, the common direction of pull forces to occur, the material of line securement body, and the diameter size of the grip channels.

Securement device 100 is an elastomeric system that uses a tension setting by way of securement strap 106 around securement body 102 that distorts the securement body 102 to then apply a compressive load generated by securement strap 106 to IV lines within the grip channels 150 in an analog, or infinitely adjustable, tension level between an open state and a closed state by holding the IV lines with a high degree of force without compressing them by way of a pinch or in a manner to disrupt fluid flow within the flexible line. Further, as mentioned above, first termination end 114 and second termination end 116 sandwich the securement flanges 150 wherein first termination end 114, second termination end 116 and flanges 150 are all located in-line with one another and configured in a curvilinear shape. This type of shape, while having ornamental and aesthetically pleasing characteristics, also allows securement body 102 to grip onto IV lines, tubes, and cords securely. This type of shape acts to carry and transmit loads (pulls or yanks on the IV lines, tubes, and cables) held in each grip channel 142 in a more uniform manner by gripping more surface area of held lines, tubes, and cables. When securement strap 106 is tightened to cause compression of the securement body 102 to surround and grip the IV lines, tubes, or cables (in grip channel 150), securement body 102 displaces significantly to a balanced shape, providing equal force applied to each line secured in each grip channel 150 around each grip channel. Securement strap 106 closes each slot 144 between each flange 150, first termination end 114, and second termination end 116, which were used to install the lines into grip channels 142 initially, causing line securement body 102 to become a more uniform oval shape (see FIG. 7B). This oval shape then transmits the securement strap 106 force to the IV lines, tubes, or cables through a physics phenomenon known as hoop stress. A cylindrical, or circular shape of body 102 would be a theoretically ideally balanced and provide the highest amount of strength on all lines in such an embodiment (depending on the width of slots 144 allowing the lines to be inserted), but is likely not comfortable on a patient, and would make for a large and awkward device to be attached based on its size or height from armband 104. In the event that a maximum amount of securement is desired, and device 100 wouldn't necessarily be flush against a patient's arm, a circular shape of securement body 102 may be desirable for the greatest ability to resist pull forces. So, a curvilinear or modified-semi-circle shape of securement body 102 combined with the armband 104 provides the best balance of manufacturability, weight, size, performance, and patient comfort for securement of lines, tubing, and cords. Alternatively, it is contemplated the curvilinear curvature in at least the XZ-plane mentioned above may be altered as desired. The greater the amount of curvature of flanges 150, first termination end 114, and second termination end 116 of securement body 102, when in its secure and compression state (securement strap 106 is tightened and securement flanges 150 overlap each other), the greater the amount of resistance can be translated onto secured IV lines with grip channels 150, tubing, or cords in the event of a line pull.

While securement body 102 is a tacky elastomer material, the key is the balance between the ease of tube insertion, safety, and comfort to the patient and the strength of device 100 to hold compression on the inserted tubes to prevent movement of the inserted tubes in securement body 102 by up to at least 9 lbs. (4.1 kg) of pull force, but preferable 20 lbs. (9.1 kg). The material properties of securement body 102 may be altered if desired for different situations. For example, in the event of a flight-for-life or military application and extra securement is desired, the shape could be changed for greater overall grip on inserted tubing, or the hardness of the material of securement body 102 could be changed to increase the strength of the grip around held lines at the expense of installation ease. In the preferred embodiment, the device 100 can withstand at least 20 lbs. (9.1 kg) of pull force in any direction (along the X, Y, or Z axis) but preferably up to 80 lbs. (36.3 kg) or more between all of the lines held by the device (assuming a force of about 10 lbs. (4.5 kg) is used to secure securement strap 106 around body 102). That is, the device would mitigate 20 lbs. (9.1 kg) of force applied to one line secured in a grip channel 142, or 5 lbs. (2.3 kg) of force applied to each of 4 lines secured in four grip channels 142. The ability of the device to withstand a pull force of 20 lbs. (9.1 kg) or more is a substantial improvement over any current solutions and has been a long-standing problem to be solved. However, it is important to note that the amount of pull force device 100 can mitigate depends on a number of factors, including, but not limited to, the securement strap 106 tension applied to securement body 102, the diameter of the cords, lines, and tubes being secured within grip channels 142, and whether the lines, tubes, and cords are rigid/stiff or flexible/pliable. In addition, the directional vector of the pull force applied to the lines, tubes, and cords and the rate of speed at which the pull force is applied can be a factor.

Figure 8:
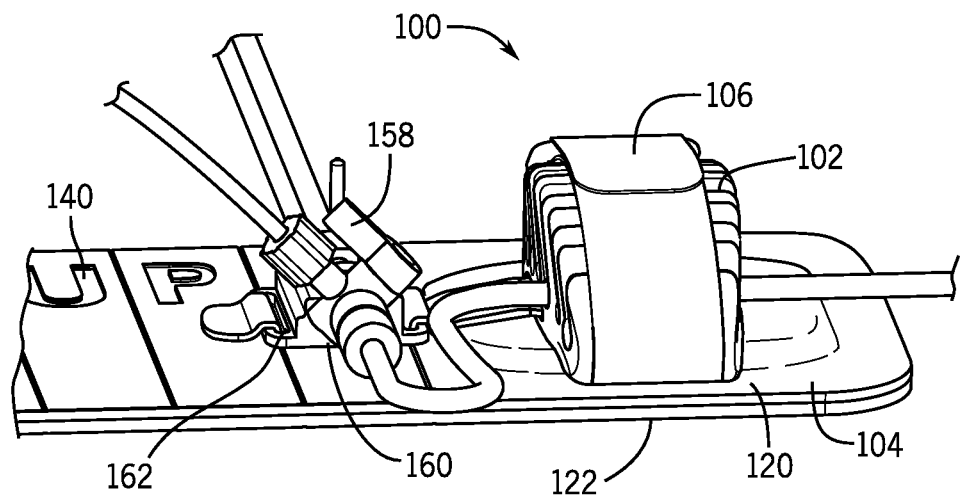
FIG. 8. is a front perspective view of an alternative embodiment of the present invention with a transducer 158 attached.
Figure 9:
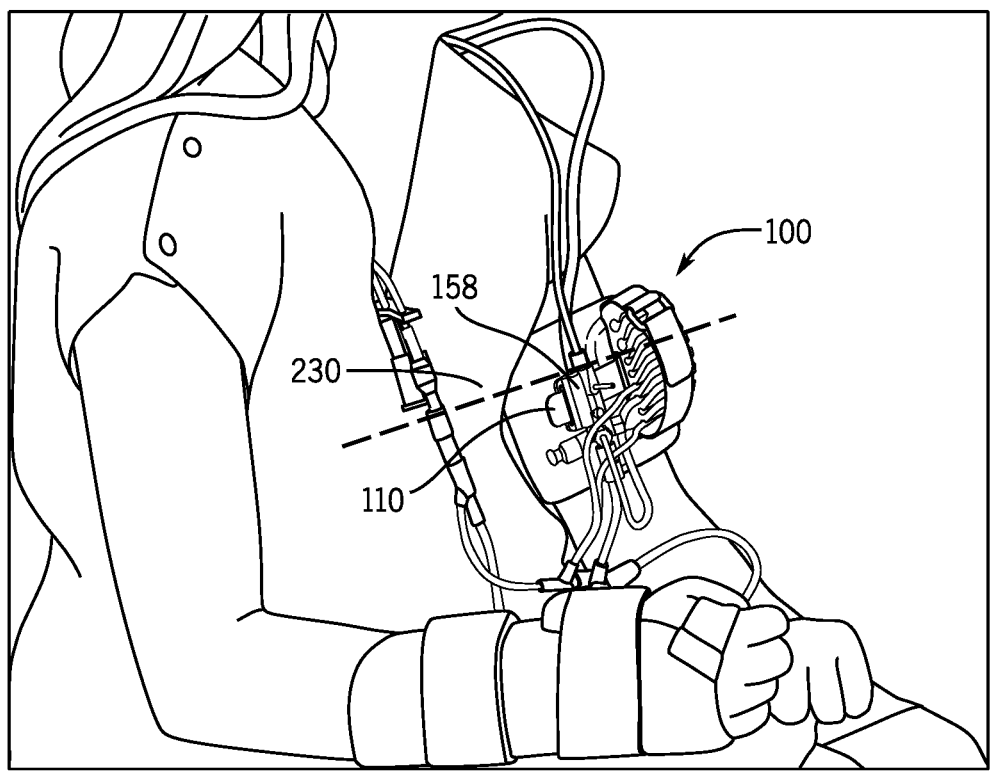
FIG. 9. is perspective view of the alternative embodiment of the present invention connected to a patient.
Figure 11:
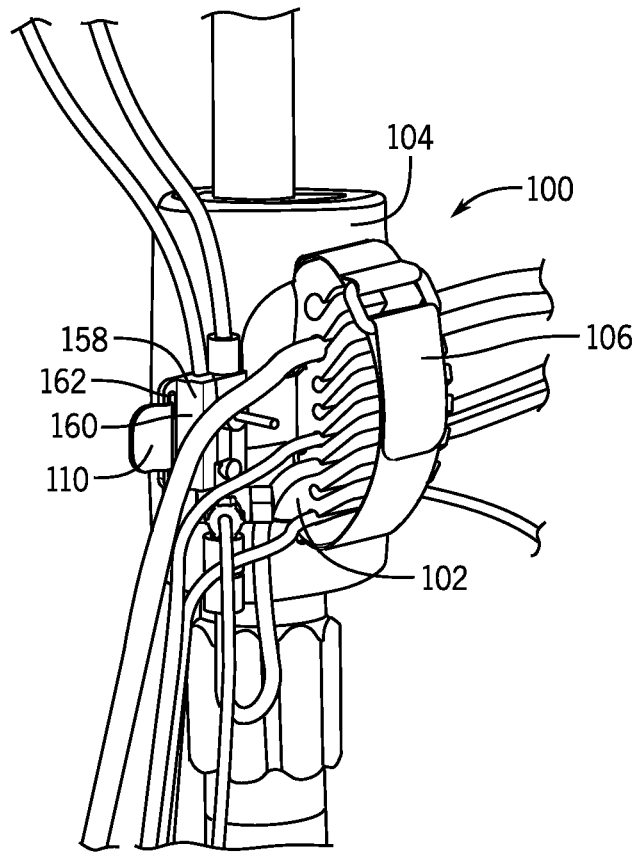
FIG. 11. is a perspective view of the alternative embodiment of the present invention secured to a stationary object.

Turning to FIG. 8 and FIG. 9, a front perspective view of an alternative embodiment of the present invention with a transducer 158 attached to upper layer 120 of armband 104 via first end 108 of strap 118, and a perspective view of the alternative embodiment of the present invention attached to a patient is shown. Transducer 158 further comprises a base 160 with at least one transducer aperture 162 located on at least one side of transducer base 160 configured to allow first end 108 of strap 118 to thread through at least one transducer aperture 162, thereby securing transducer 158 to upper layer 120 via hook fastener of first end 108 affixing to loop fastener on top surface 134 of upper layer 120 of armband 104. First end 108 of strap 118 is presently configured to secure up to 3 transducers 158 in-line with one another to armband 104, however first end 108 may be made longer or shorter to accommodate a different quantity of transducers 158 or other desirable devices to be secured to securement device 100. Turning to FIG. 11, the location and position of first end 108 of strap 118 is important for transducer use as each transducer 158, via armband 104 placement on a patient, device 100 allows correct positioning of transducer 158 to be in-line or level with the right atrium of a patient's heart 230 (see dotted line), which is critical for correct monitoring of life support medications via transducer 158 based on real-time blood pressure readings. Transducers were designed to be placed on IV poles but are more commonly attached to patient gowns with a clothespin, or taped to their arm, or through using a product that was intended to hold catheters in place on a patient's legs, which unfortunately falls down the patient's arm regularly, causing unnecessary potentially life-threatening disruptions. None of these methods can appropriately secure the transducer in the correct position as mentioned above by device 100, which is crucial for proper hemodynamic monitoring after operations such as open-heart surgery or transplants.

Figure 10:
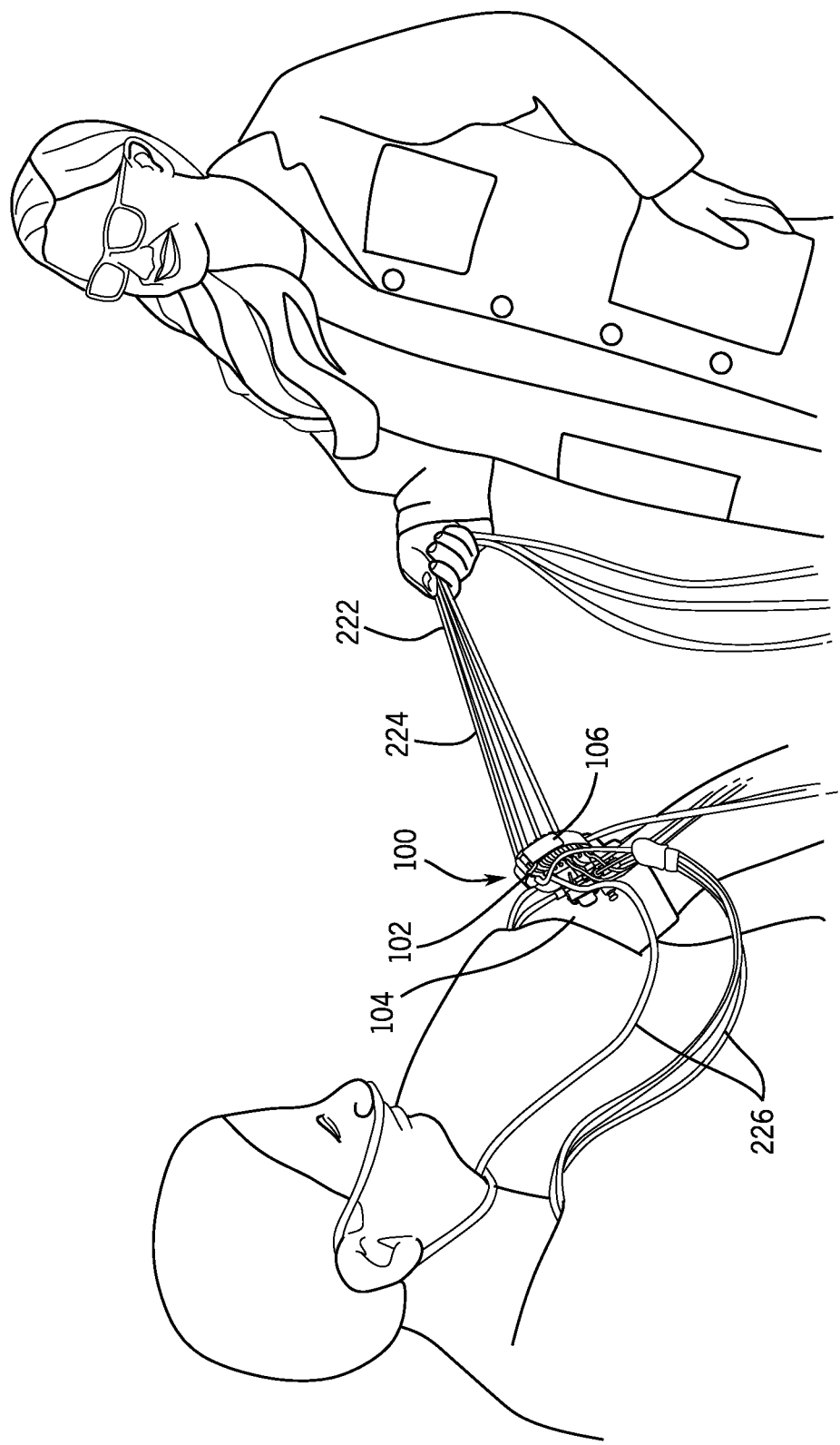
FIG. 10. a perspective view of the alternative embodiment of the present invention connected to a patient.

Turning to FIG. 10 and FIG. 11, a perspective view of the alternative embodiment of the present invention connected to a patient and secured to a stationary object is shown. Ultimately, medical line tension mitigation securement device 100 is a tension mitigation, or strain relief, device and system, where the device translates tension in the IV lines from a force vector, such as a yank or tug, to device 100 on the patients arm and not to the IV-line insertion site into the patient, providing a unique ability to prevent painful line pulling and dangerous dislodgement at patient insertion site(s). An example of this is illustrated in FIG. 10 where device 100 separates at least one line 222 (four lines in the current embodiment) attached to a patient into a load side 224 and a secure side 226. When the lines on load side 224 of device 100 experience a force vector, such as a tug, device 100 absorbs and translates the force vector to the patient's arm instead of transferring to the secure side 226 of the lines, which are connected to patient insertion sites (locations where a line is attached to or extends into a patient's skin or body), thereby potential preventing pain and injury to the patient from the force vector. When secured lines 222 are not under load, securement device 100 is still constantly applying a compressive grip force to lines 222 that the patient does not feel. That is, a compression load, via securement strap 106, is constantly being applied to hold the IV lines 222 in place by securement body 102, and that compression load is independent of armband 104 surrounding the patient's arm, ensuring device 100 is always ready to protect against a tug or yank. That is, the compression load on body 102 is independent (and can be adjusted independently) of the force used to tighten armband 104 around the patient's arm. The compression load on securement body 102 from securement strap 106 forces securement body 102 into an oval shape which promotes even distribution of compression load on any secured lines 222 around the circumference of each line 222, ensuring a strong grip on each line 222. However, when an external tension or pull force is applied to lines 222 secured within body 102, that load is translated to the securement body 102 performing the compression load onto the lines, which is translated onto armband 104, which is then transferred to the patient arm (or other secure structure). Turning to FIG. 11, device 100 is secured around a pole, such as an IV pole, via armband 104.

Figure 12A:
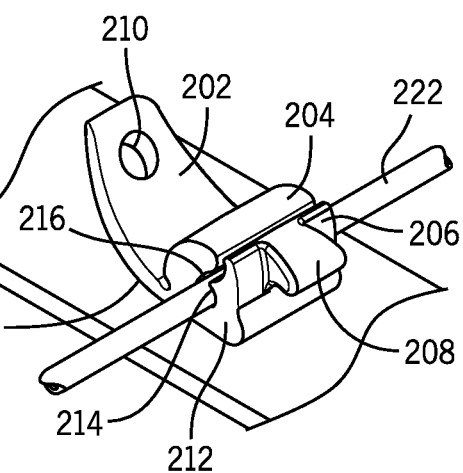
FIG. 12A. is a perspective view of another alternative embodiment of the present invention in an open position.
Figure 12B:
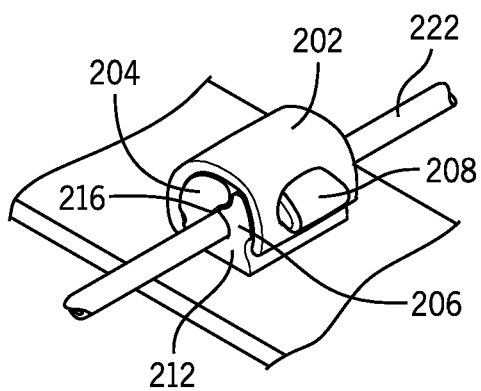
FIG. 12B. is a perspective view of another alternative embodiment of the present invention in a closed position.

Turning to FIG. 12A and FIG. 12B, a perspective view of another alternative embodiment of the present invention in an open and a closed (or compression) position is shown. In this alternative embodiment, armband 104 may comprise one or more individual securement bodies 200, secured to armband 104 in the same manner as securement body 102 (via sandwiching a first and second protrusion (not shown) located on the base 212 of body 200 between upper layer 120 and lower layer 122 of armband 104). Securement body 200 comprises a base 212 with a securement strap 202 formed integral to securement body 200 (replacing securement strap 106 on the previous embodiment), a single securement flange 204 and a single termination end 206 forming a grip channel 214 and a slot 216, wherein securement strap 202, securement flange 204, and termination end 206 are all connected to base 212. Termination end 206 further comprises a protrusion 208 extending away from securement flange 204. Securement strap 202 further comprises at least one opening 210 formed therethrough and configured to secure over protrusion 208, which is essentially a hook feature to hold onto opening 210. Varied tension may be applied to securement body 200 by securing different openings 210, where an opening 210 formed closer to where securement strap 202 is connected to base 212 would yield greater tension on securement body 200 and an opening 210 formed in securement strap 202 formed further away from base 212 would yield reduced tension on securement body 202. Such an embodiment allows for a single line to be removed or adjusted in a particular securement body 200 without affecting the tension of any adjacent securement bodies 200, or the lines they secure, should multiple securement bodies 200 be located on a single armband 104. In the open position, a line may be placed into grip channel 214 via slot 216. In the closed position, line is secured in grip channel 214 when securement strap 202 overlaps securement flange and termination end 206, thereby positioning opening 210 of strap 202 over protrusion 208 of termination end 206, thereby providing tension on securement body 200 and any held line in grip channel 214. In addition, in any embodiment, it is contemplated the width of each slot 216 of securement body 202 could be increased or modified in conjunction with modification to the shape or material choices of body 202 to allow easier insertion of IV lines, tubing, or cords to be placed in a grip channel 214.

Figure 13:
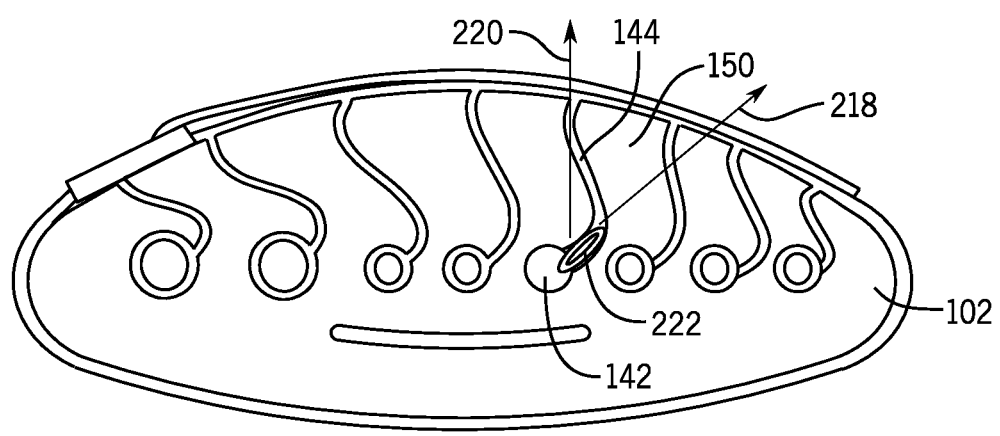
FIG. 13. is a left side view of an alternative embodiment of body 102.

Turning to FIG. 13 a left side view of alternative embodiment of body 102 (without first first protrusion 130 or second protrusion 132 shown and after securement strap 106 is under tension) is shown. In this embodiment securement flanges 150 and slots 144 could be configured to be curved, in a "torturous path" type of slot. Such a configuration could prevent line 222 held in grip channel 142 from being pulled in a straight direction out of grip channel 142 and slot 144, which is the path of least resistance in the event of a force vector 218 or 220 in that direction. Knowing force vectors are typically linear and are being pulled from a constant location and position, a curved flange 150 and slot 144 configuration would significantly decrease the likelihood of a line pulling straight through a straight (whether vertical or angled slot). A curved or zig-zag shape of slot 144 would be a secondary defense against the pulling of line 222 straight up and out of body 102 with the "pinching" affect and friction being applied to the line to keep it in place while the line is under tension. If a line pulls through slot 144 and is under load against securement strap 106, it will otherwise have an insignificant load reduction capacity during a significant line pull force. After such line pull incidents, the armband shall be inspected to ensure the lines are back in their proper grip channels.

A method to use securement device 100 begins first with configuring device 100 with at least one slot 144, at least one flange 150, a first termination end 114, a second termination end 116, and a securement strap 106 around a securement body with each slot 144 on securement body 102 facing up or toward the sky. Next, medical tubes, IV lines, and/cords are inserted into the grip channel 142 of securement body 102 that most closely resemble the size of the line diameter (device 100 is in an open state). Next, securement strap 106 is fastened and tightened, causing each flange 150 to touch the neighboring flange 150 or second termination end 116 (device 100 is in a closed position). Also, in the event of a catastrophic or adverse load applied to device 100, if and when a line is in this position shown by line 222 or in any of the embodiments mentioned, fluid flow and drug delivery to the patient via the line will not be altered or compromised as the line is not pinched fully based on the design, shape, size, and materials of device 100 as described in this application.

While the present invention has been described above in terms of specific embodiments, it is to be understood that the invention is not limited to these disclosed embodiments. Many modifications and other embodiments of the invention will come to mind of those skilled in the art to which this invention pertain, and which are intended to be and are covered by both this disclosure and the appended claims. It is indeed intended that the scope of the invention should be determined by proper interpretation and construction of the appended claims and their legal equivalents, as understood by those of skill in the art relying upon the disclosure in this specification and the attached drawings. Likewise, where this document refers to technologies that would be apparent or known to one of ordinary skill in the art, such technologies encompass those apparent or known to the skilled artisan now or at any time in the future.

The invention claimed is:

1. A securement device comprising:
   a securement band;
   a securement body including a top surface, a bottom surface, a first side surface and a second side surface, wherein the securement body is attached to the securement band and configured to secure at least a portion of at least one tube, line, or cord; and
   a securement strap in contact with the top surface, the bottom surface, the first side surface, and the second side surface of the securement body, wherein the securement strap applies an increasing level of tension to the securement body as the securement strap is tightened around the securement body,
   wherein the top surface, the bottom surface, the first side surface, and the second side surface are parallel to a length of the portion of the at least one tube, line, or cord, and deform into a convex shape around the portion of the at least one tube, line, or cord when the securement body is under tension from the securement strap to provide a compressive load to the portion of the at least one line, tube, or cord to secure the portion from movement due to a pull force.

2. The device of claim 1 wherein the securement body is configured, when under tension, to provide a near uniform compressive load around a circumference of the secured portion of the at least one line, tube, or cord.

3. The device of claim 1 wherein the securement body, when under tension, is configured to absorb and transmit a force applied to the secured portion of the at least one line, tube, or cord to the securement band.

4. The device of claim 1 wherein the securement device further comprises a strap which extends through the securement body.

5. The device of claim 1 wherein the securement band is further comprised of an upper layer with an aperture formed therethrough and a lower layer, wherein a portion of the securement body is secured between the upper layer and lower layer and the securement strap is slidable along the bottom surface of the securement body.

6. The device of claim 5 wherein the securement body extends partially through the aperture in the upper layer.

7. The device of claim 5 wherein the lower layer is comprised of a USP Class VI medical grade material.

8. The device of claim 1 wherein the securement strap is configured to surround the securement body along a plane.

9. A securement device comprising:
   a securement band;
   a securement body attached to the securement band and further comprising at least one grip channel formed therethrough that is configured to hold at least one tube, line or cord;
   a securement strap located around the securement body, and is configured to apply an increasing level of tension to the securement body as the securement strap is tightened,
   wherein the securement body, when under tension, deforms to generate a near uniform hoop stress around the at least one grip channel to prevent at least a portion of the at least one tube, line or cord held by the securement body from moving within the securement body due to more than one successive pull force of at least 15 lbs. (6.8 kg).

10. The device of claim 9 wherein the securement body further comprises:
    a unitary base;
    a strap aperture formed therethrough the base and configured to operate with a strap;
    at least one flange connected to the base and the at least one grip channel; and
    at least one termination end,
    wherein the at least one flange and a second flange or at least one termination end define a slot connected to the at least one grip channel.

11. The device of claim 10 wherein the at least one flange is at an angle between 20 and 50 degrees in relation to the base.

12. The device of claim 10 wherein the securement body further comprises:
    a first protrusion extending from the base; and
    a second protrusion extending from the base,
    wherein the first protrusion and second protrusion are configured to attach the securement body to the securement band.

13. The device of claim 10 wherein one end of the strap is configured to secure at least one transducer to the securement band and to extend through the strap aperture.

14. The device of claim 13 wherein the strap is further configured to maintain the at least one transducer in-line with the heart of a patient when the securement band is secured to an arm of the patient.

15. The device of claim 9 wherein the securement body is comprised of a tacky elastomer.

16. The securement device of claim 9 wherein the securement device further comprises a strap attached to the securement band and configured to secure the securement band around a secure structure.

17. The securement device of claim 9 wherein the securement strap is in communication with a surface of the securement body.

18. A method for securing a tube, line, or cord to a securement device comprising: Securing to a secure structure a securement band comprising a securement strap and a securement body with at least one grip channel where each grip channel is defined by either two flanges or one flange and one termination end, wherein the two flanges or the one flange and the one termination end each further comprises a top surface; inserting at least a portion of the tube, line, or cord into the at least one grip channel; and tightening the securement strap around the securement body so the securement strap comes into contact with each top surface of the two flanges or the one flange and the one termination end, causing the securement body to deform to generate hoop stress around the at least one grip channel which prevents at least the portion of the tube, line, or cord from movement.

19. The method of claim 18 wherein a diameter of the at least one grip channel closely matches an outer diameter of the tube, line, or cord.

20. The method of claim 18 wherein a portion of the securement body forming the at least one grip channel compresses around a circumference of the tube, line, or cord.

21. The method of claim 18 wherein the securement device further comprises a strap.

22. A securement device comprising:
    a securement band configured to removably attach to a secure structure;
    a securement body attached to the securement band and configured to secure at least one line, tube or cord, the securement body attached to the securement band and further comprises a surface defining a perimeter around the securement body; and a securement strap in contact with the surface all the way around the perimeter of the securement body, wherein the securement body is configured, when under tension by the securement strap, to separate the at least one line, tube or cord into a load side and a secure side, the securement body being configured to transfer more than one pull force applied to the load side of the at least one line to the securement body and the secure structure instead of to the secure side of the at least one line, tube, or cord.

23. The securement device of claim 22, wherein the securement band can be tightened and adjusted independently from, the securement strap.

24. The securement device of claim 22 wherein the securement strap is made integral with the securement body.

* * * * *